United States Patent [19]

Spector et al.

[11] 3,984,348
[45] Oct. 5, 1976

[54] POLYOLEFIN LIGHT STABILIZERS

[75] Inventors: Richard Spector, Kendall Park; Joseph Anthony Stretanski, Clinton, both of N.J.

[73] Assignee: American Cyanamid Company, Stamford, Conn.

[22] Filed: Apr. 7, 1975

[21] Appl. No.: 565,884

Related U.S. Application Data

[60] Division of Ser. No. 412,922, Nov. 5, 1973, Pat. No. 3,925,518, which is a continuation-in-part of Ser. No. 351,043, April 13, 1973, Pat. No. 3,923,733.

[52] U.S. Cl. ............................. 252/400 A; 252/402; 252/404; 260/45.9 NP; 260/45.95 F
[51] Int. Cl.² .................. C09K 15/32; C09K 15/26; C09K 15/08; C08K 5/05
[58] Field of Search ...... 260/959, 45.9 NP, 45.95 F; 252/400 A, 406, 402, 404

[56] References Cited
UNITED STATES PATENTS

| | | | |
|---|---|---|---|
| 2,615,037 | 10/1952 | Moyle | 260/959 |
| 2,615,038 | 10/1952 | Moyle | 260/959 |
| 2,994,638 | 8/1961 | Malz | 260/959 |
| 3,038,924 | 6/1962 | Schoot | 260/959 |
| 3,218,294 | 11/1965 | Rodgers | 260/45.75 N |
| 3,260,712 | 7/1966 | Schrader | 260/949 |
| 3,359,233 | 12/1967 | Mirviss | 260/45.9 NP |
| 3,491,057 | 1/1970 | Kato | 260/45.8 N |
| 3,641,213 | 2/1972 | Rodgers | 260/895 |
| 3,702,878 | 11/1972 | Saito | 252/400 A |
| 3,923,733 | 12/1975 | Spector | 260/959 |
| 3,925,518 | 12/1975 | Spector | 260/959 |

*Primary Examiner*—Samuel W. Engle
*Assistant Examiner*—Donald P. Walsh
*Attorney, Agent, or Firm*—Philip Mintz

[57] ABSTRACT

O,O-Bis(aryl)amidothiophosphates, useful as light stabilizers in polyolefins, are those having the formula:

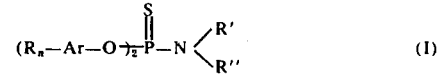

wherein: R is hydrogen, alkyl of 1–12 carbons, or halogen; Ar is phenyl or naphthyl; $n$ is 1 or 2; and R' and R'', which may be the same or different, are each selected from the group consisting of hydrogen, alkyl of 1–18 carbons, 2,2,6,6-tetramethyl-4-piperidyl, cycloalkyl of 5–6 carbons or both R' and R'', together with the N to which they are attached, form a morpholino or piperidino ring. Such compounds are made by reacting $PSCl_3$ with two moles of a phenol and then the product thereof with an amine.

6 Claims, No Drawings

POLYOLEFIN LIGHT STABILIZERS

This application is a division of application Ser. No. 412,922, filed Nov. 5, 1973, now U.S. Pat. No. 3,925,518, which application was a continuation-in-part of application Ser. No. 351,043, filed Apr. 13, 1973, now U.S. Pat. No. 3,923,733.

This invention relates to stabilizing polyolefins against the deteriorating effects of light by the use of certain O,O-bis(aryl)amidothiophosphates, alone or in combination with a 2-hydroxy-4-alkoxybenzophenone, and to certain novel O,O-bis(phenyl)amidothiophosphate compounds.

As is well known, polyolefins such as polypropylene and polyethylene tend to deteriorate from the effects of light, especially ultraviolet light. This deterioration generally manifests itself as a loss of tensile strength and loss of flexibility of the polymer.

In accordance with the present invention, we have discovered that certain O,O-bis(aryl)amidothiophosphates, alone or in combination with a 2-hydroxy-4-alkoxybenzophenone, can significantly retard or inhibit such deterioration.

The O,O-bis(aryl)amidothiophosphates useful for the practice of the present invention include those having the formula:

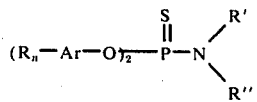
(I)

wherein: R is hydrogen, alkyl of 1–12 carbons, or halogen; Ar is phenyl or naphthyl; $n$ is 1 or 2; and R' and R'', which may be the same or different, are each selected from the group consisting of hydrogen, alkyl of 1–18 carbons, 2,2,6,6-tetramethyl-4-piperidyl, cycloalkyl of 5–6 carbons or both R' and R'', together with the N to which they are attached, form a morpholino or piperidino ring. Within this class of compounds, those which are preferred since they give better light stability to polyolefins are the compounds of the formula:

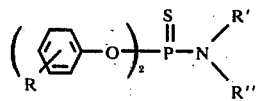
(II)

wherein: R is hydrogen, alkyl of 1–12 carbons, or halogen; R' and R'', which may be the same or different, are each selected from the group consisting of hydrogen, cyclohexyl, or 2,2,6,6-tetramethyl-4-piperidyl. Especially preferred, since they give the best light stability to polyolefins, are the novel compounds of the formula:

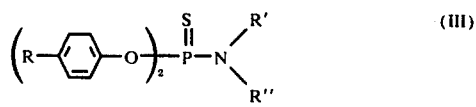
(III)

wherein: R is alkyl of 1–6 carbons or halogen; R' is cyclohexyl or 2,2,6,6-tetramethyl-4-piperidyl; and R'' is hydrogen or R'.

As a broad class, amidophosphates are known compounds as shown in such references as U.S. Pat. Nos. 3,100,197; 3,309,317; and 3,531,550, British Pat. Nos. 941,575 and 1,039,924, and Kosolapoff "Organophosphorous Compounds" (1950) pages 278–324. Such broad class of amidophosphates may be represented by the formula:

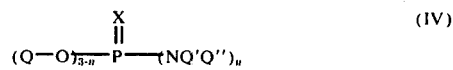
(IV)

wherein: Q, Q', and Q'' represent hydrogen or organic moieties, $n$ is 1, 2, or 3, and X is oxygen or sulfur. In accordance with our invention, we have discovered that only a very small segment of this broad class contains compounds useable alone or in combination with a 2-hydroxy-4-alkoxybenzophenone to stabilize polyolefins against deterioration by light. The compounds of this small segment, having the structural formulae (I), (II), or (III), supra, have certain structural features in common. First, the X of formula (IV) must be sulfur; compounds wherein the X is oxygen are greatly inferior or even inoperative as light stabilizers in polyolefins. Second, $n$ of formula (IV) must be one; the diamides and triamides are greatly inferior as light stabilizers in polyolefins. Third, the Q of formula (IV) should be aromatic and the Q' and Q'' should not be aromatic since compounds wherein Q is aliphatic and compounds wherein Q' or Q'' is aromatic are inferior for this purpose.

The compounds of formula (IV), supra, can be prepared in several ways, one of which is described generically in U.S. Pat. No. 3,531,550 (columns 3 and 4). To make the specific compounds of formulae (I), (II), or (III), supra, the appropriate phenol can be reacted with thiophosphoryl chloride in the presence of an HCl-acceptor or base to give an intermediate which can then be reacted with the appropriate amine to give the desired O,O-bis(aryl)amidothiophosphate, according to the following reaction sequence:

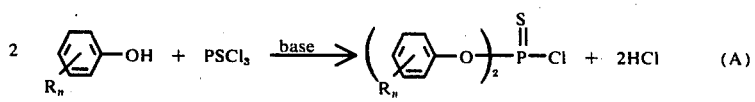
(A)

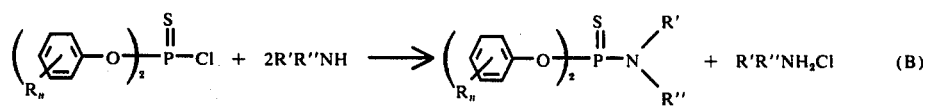
(B)

To make the compounds of formulae (I), (II), or (III), supra, suitable monohydroxy-phenols include phenol, methylphenols or cresols, ethylphenols, propylphenols, butylphenols, hexylphenols, octylphenols, nonylphenols, decylphenols, dodecylphenols, dimethylphenols or xylenols, isopropylmethyl-phenol or thymol, di-tert- .butylphenols, chlorophenols, methylclorophenols, naphthols, methylnaphthols, ethylnaphthols, chloronaphthols, etc. Preferably, where the phenol has one substituent, such substituent is in the para position. Suitable amines include ammonia, methylamine, ethylamine, propylamines, butylamines, hexylamines, octylamines, dodecylamines, octadecylamines, cyclopentylamine, cyclohexylamine, 4-amino-2,2,6,6-tetramethylpiperidine, morpholine, piperidine, dimethylamine, dibutylamines, dioctylamines, methylbutylamine, methylcyclohexylamine, dicyclohexylamine, etc.

The compounds of formulae (I), (II), and (III), supra, when incorporated alone in polyolefins significantly inhibit degradation due to exposure to light. This effect can be greatly enhanced if a 2-hydroxy-4-alkoxybenzophenone, a 2-(2'-hydroxyphenyl)benzotriazole, a nitroxide, a tetramethylpiperidine derivative, or a 3,5-ditert.butyl-4-hydroxybenzoate is also incorporated in the polyolefin. Illustrative of such enhancing compounds are those mentioned in such prior art as U.S. Pat. Nos. 3,189,615; 3,206,431; 3,230,194; 3,431,232; 3,431,233; 3,436,369; 3,448,074; 3,474,068 and 3,640,928. Such enhancing compounds include 2-hydroxy-4-methoxybenzophenone, 2-hydroxy-4-butoxybenzophenone, 2-hydroxy-4decyloxybenzophenone, 2-hydroxy-4-dodecyloxybenzophenone, 2,2'-dihydroxy-4,4'-dimethoxybenzophenone, and 2,2'-dihydroxy-4-methoxybenzophenone, 2-(2'-hydroxy-5'-methylphenyl)benzotriazole, 2-(3'-tert.butyl-2'-hydroxy-5'-methylphenyl)-5-chlorobenzotriazole, 2-(3',5'-ditert.butyl-2'-hydroxyphenyl)-5-chlorobenzotriazole, 2-(2'-hydroxy-5'-tert.octylphenyl)benzotriazole, 2,2,5,5-tetramethyl-4-oxoimidazolidine-1-oxide, cyclohexane-1-spiro-2'-(4'-oxoimidazolidine-1'-oxide)-5'-spiro-1''-cyclohexane, 2,2,6,6-tetramethyl-4-(α-cyano-α-ethoxycarbonylmethylene)piperidine-1-oxide, 1,3,8-triaza-7,7,9,9-tetramethyl-2,4-dioxo-spiro[4,5]decane-8-oxyl, 2,2,6,6-tetramethyl-4-n-butyliminopiperidine-1-oxide, benzimidazoline-2-spiro-4'-(2',2',6',6'-tetramethylpiperidine-1'-oxide), 4-stearoyloxy-2,2,6,6-tetramethylpiperidine, 4-(p-chlorobenzoyloxy)-2,2,6,6-tetramethylpiperidine, 4-(ethylcarbamoyloxy)-2,2,6,6-tetramethylpiperidine, bis(2,2,6,6-tetramethyl-4-piperidyl)adipate, 2,4-ditert.butylphenyl 3,5-ditert.butyl-4-hydroxybenzoate, octadecyl 3,5-ditert.butyl-4-hydroxybenzoate, although 2-hydroxy-4-octyloxybenzophenone, commercially available as Cyasorb UV-531, is preferred and is used in the following examples as exemplary of this class.

When used alone, or in combination with a 2-hydroxy-4-alkoxybenzophenone, the O,O-bis(aryl)amidothiophosphate is usually incorporated into the polyolefin at a concentration of 0.1 to 2% by weight, preferably at a concentration of 0.2 to 0.5% on weight of polyolefin. When used with the enhancer, the ratio of the O,O-bis(aryl)amidothiophosphate to the 2-hydroxy-4-alkoxy-benzophenone may be between 10/1 and 1/10, although a ratio of about 1/1 is usually preferred. Further enhancement is oftentimes obtained when the O,O-bis(aryl)amidothiophosphate or the combination thereof with the 2-hydroxy-4-alkoxybenzophenone is used with a phosphite, such as cyclic phosphites as disclosed in U.S. Pat. No. 3,205,250, especially distearylpentaerythritol diphosphite; tris(p-nonylphenyl)phosphite; alkyl phosphites, such as dioctylphosphite and tridecylphosphite; alkyl aryl phosphites, such as phenyl didecyl phosphite; aryl o-phenylene phosphites, such as phenyl or 4-methyl-2,6-di-t-butylphenyl o-phenylene phosphite, and the like. Other additives, such as processing antioxidants, secondary stabilizers such as dilauryl- or distearyl-thiodipropionate, pigments, dyes, flame retardants, lubricants, etc. may also be included in the polyolefin for their usual purposes.

For further illustration of this invention, reference should be made to the following examples.

EXAMPLE 1

Preparation of O,O-bis(p-tert.butylphenyl)-N-cyclohexylamidothiophosphate

To a solution of cyclohexylamine (20 grams, 0.2 mole) in 10 milliliters of dimethylformamide and 50 milliliters of benzene at 50°–60°C. was added dropwise, with stirring, a solution of O,O-bis(p-tert.butylphenyl)-chlorothiophosphate (20 grams, 0.05 mole) in 100 milliliters of benzene. The mixture was refluxed for 8 hours, cooled, and filtered. The filtrate was evaporated under reduced pressure, and the oil that remained was triturated with cold methanol. The solid which formed was filtered and recrystallized twice from methanol to give 17.6 grams of product, m.p. 107°–109°C.

EXAMPLE 2

Testing in Polypropylene

The compound of Example 1 (0.5% by weight) was dry blended with a mastermix of unstabilized polypropylene (Profax 6401) and 0.2% by weight of a processing antioxidant, 2,4,6-tritert.butylphenol. The blend was milled for five minutes at 350°–370°F. and the milled sample was compression molded into a film 4–5 mils thick at 400°F. The compression molded film, and a control film identically prepared except without the compound of Example 1, were exposed in a Xenon Weather-O-Meter (Atlas) until they failed. The samples were considered as having failed when the carbonyl content in the infrared spectrum reached 0.1%, a generally accepted point of film embrittlement. The test sample lasted 1300 hours longer than the control, representing a life of 3.6 times that of the control.

EXAMPLES 3–20

In the manner of Example 1, using the appropriate amines and appropriate O,O-bis(phenyl)chlorothiophosphates, additional compounds were prepared and tested as in Example 2. The compounds and the test results are described below.

Example 3 — dicyclohexylamine reacted with O,O-bis(p-tert.butylphenyl)chlorothiophosphate to yield O,O-bis(p-tert.butylphenyl)-N,N-dicyclohexylamidothiophosphate, m.p. 208°–212°C. which, in the polypropylene test sample, lasted 800 hours longer than the control, representing a life of 2.6 times that of the control.

Example 4 — cyclohexylamine reacted with O,O-bis(p-methylphenyl)chlorothiophosphate to yield O,O-bis(p-methylphenyl)-N-cyclohexylamidothiophosphate, a liquid, which, on testing, lasted 600 hours longer than the control, representing a life of 2.5 times that of the control.

Example 5 — cyclohexylamine reacted with O,O-bis(p-chlorophenyl)chlorothiophosphate to yield O,O-bis(p-chlorophenyl)-N-cyclohexylamidothiophosphate, m.p. 65°–67°C. which, on testing, lasted 900 hours longer than the control, representing a life of 3.25 times that of the control.

Example 6 — cyclohexylamine reacted with O,O-bis(p-tert.octylphenyl)chlorothiophosphate to yield O,O-bis(p-tert.octylphenyl)-N-cyclohexylamidothiophosphate, m.p. 80°–82°C. which, on testing, lasted 400 hours longer than the control, representing a life of 1.62 times that of the control.

Example 7 — cyclohexylamine reacted with O,O-bis-(2,4-di-tert.butylphenyl)chlorothiophosphate to yield O,O-bis(2,4-di-tert.butylphenyl)-N-cyclohexylamidothiophosphate, m.p. 167°–168°C. which, on testing, lasted 650 hours longer than the control, representing a life twice that of the control.

Example 8 — cyclohexylamine reacted with O,O-bis(phenyl)chlorothiophosphate to yield O,O-bis(-phenyl)-N-cyclohexylamidothiophosphate, m.p. 76°–77°C. which, on testing, lasted 750 hours longer than the control, representing a life of 2.15 times that of the control.

Example 9 — cyclohexylamine reacted with O,O-bis(n-butyl)chlorothiophosphate to yield O,O-bis(n-butyl)-N-cyclohexylamidothiophosphate, a liquid, which, on testing, lasted only 300 hours longer than the control. This compound is outside the scope of this invention.

Example 10 — cyclohexylamine reacted with O,O-bis(p-methoxyphenyl)chlorothiophosphate to yield O,O-bis(p-methoxyphenyl)-N-cyclohexylamidothiophosphate, m.p. 59°–61°C. which, on testing, lasted only 100 hours longer than the control. This compound is outside the scope of this invention.

Example 11 — p-tolylamine reacted with O,O-bis(p-tert.butylphenyl)chlorothiophosphate to yield O,O-bis(p-tert.-butylphenyl)-N-p-tolylamidothiophosphate, m.p. 199°–202°C. which, on testing, lasted 400 hours longer than the control, representing a life of only 1.5 times that of the control. This compound is outside the scope of this invention.

Example 12 — aniline reacted with O,O-bis(p-tert.-butylphenyl)chlorothiophosphate to yield O,O-bis(p-tert.butylphenyl)-N-phenylamidothiophosphate, m.p. 162°–164°C. which, on testing, lasted only 150 hours longer than the control. This compound is outside the scope of this invention.

Example 13 — 4-amino-2,2,6,6-tetramethylpiperidine reacted with O,O-bis(p-tert.butylphenyl)chlorothiophosphate to yield O,O-bis(p-tert.butylphenyl)-N-(2,2,6,6-tetramethyl-4-piperidyl)amidothiophosphate, m.p. 131°–133°C. which, on testing, lasted 900 hours longer than the control, representing a life of 3.25 times that of the control.

Example 14 — morpholine reacted with O,O-bis(p-tert.-butylphenyl)chlorothiophosphate to yield O,O-bis(p-tert.butylphenyl)-N-oxydiethyleneamidothiophosphate, m.p. 110°–112°C. which, on testing, lasted 650 hours longer than the control, representing a life twice that of the control.

Example 15 — ammonia reacted with O,O-bis(p-sert.butylphenyl)chlorothiophosphate to yield O,O-bis(p-tert.butylphenyl)amidothiophosphate, m.p. 128°–129°C. which, on testing, lasted 700 hours longer than the control, representing a life 2.75 times that of the control.

Example 16 — di-n-butylamine reacted with O,O-bis(p-tert.butylphenyl)chlorothiophosphate to yield O,O-bis(p-tert.butylphenyl)-N,N-di-n-butylamidothiophosphate, a liquid, which, on testing lasted 400 hours more than the control, representing a life of 1.5 times that of the control.

Example 17 — n-butylamine reacted with O,O-bis(p-tert.butylphenyl)chlorothiophosphate to yield O,O-bis(p-tert.-butylphenyl)-N-a-butylamidothiophosphate, m.p. 78°–80°C. which, on testing, lasted 650 hours longer than the control, representing a life of twice that of the control.

Example 18 — tert.butylamine reacted with O,O-bis(p-tert.butylphenyl)chlorothiophosphate to yield O,O-bis(p-tert.butylphenyl)-N-tert.butylamidothiophosphate, m.p. 75°–77°C. which, on testing, lasted 550 hours longer than the control, representing a life of 1.85 times that of the control.

Example 19 — n-octylamine reacted with O,O-bis(p-tert.butylphenyl)chlorothiophosphate to yield O,O-bis(p-tert.butylphenyl)-N-n-octylamidothiophosphate, m.p. 33°–37°C. which, on testing, lasted 550 hours longer than the control, representing a life of 1.85 times that of the control.

Example 20 — cyclohexylamine reacted with O-(p-tert.butylphenyl)dichlorothiophosphate to yield O-(p-tert.butylphenyl)-N,N'-dicyclohexyldiamidothiophosphate, m.p. 114°–116°C. which, on testing, lasted only 150 hours longer than the control. This compound is outside the scope of this invention.

EXAMPLE 21

Following the procedure of Example 2, films were prepared containing 0.25% of the compound of one of the foregoing examples in combination with 0.25% 2-hydroxy-4-octyloxybenzophenone (Cyasorb UV-531) and tested with the results shown in the following table.

| Compound of Example | Hours to Failure |
| --- | --- |
| 1 | 2200 |
| 3 | 3000 |
| 7 | 2200 |
| 8 | 2100 |
| 14 | 2100 |
| 17 | 2000 |
| 19 | 2200 |

For comparison, a control (without either additive) only lasted 500 hours, and a film containing 0.5% of the 2-hydroxy-4-octyloxybenzophenone without any amidothiophosphate only lasted 1700 hours.

We claim:
1. A stabilizer composition useful for stabilizing polyolefins against the deteriorating effects of light, comprising, in combination, a 2-hydroxy-4-alkoxybenzophenone and a compound of the formula:

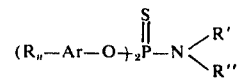

wherein:
R is hydrogen, alkyl of 1–12 carbons, or halogen;
Ar is phenyl or naphthyl;
n is 1 or 2; and
R' and R" are each selected from the group consisting of hydrogen, alkyl of 1–18 carbons, 2,2,6,6-tetramethyl-4-piperidyl, cycloalkyl of 5–6 carbons, or both, together with the N, form a heterocyclic ring selected from morpholino or piperidino.

2. A stabilizer composition as defined in claim 1 wherein said compound has the formula

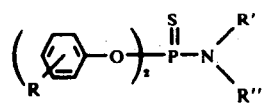

wherein:
R is hydrogen, alkyl of 1–12 carbons, or halogen; and
R' and R" are each selected from the group consisting of hydrogen, 2,2,6,6-tetramethyl-4-piperidyl, or cyclohexyl.

3. A stabilizer composition as defined in claim 2 wherein:
R is alkyl of 1–6 carbons or halogen
R' is cyclohexyl or 2,2,6,6-tetramethyl-4-piperidyl; and
R" is hydrogen or R'

4. A stabilizer composition as defined in claim 3 wherein said compound is O,O-bis(p-tert.butylphenyl)-N-cyclohexylamidothiophosphate.

5. A stabilizer composition as defined in claim 4 wherein said 2-hydroxy-4-alkoxybenzophenone is 2-hydroxy-4-octyloxybenzophenone.

6. A stabilizer composition as defined in claim 1 wherein the ratio of said 2-hydroxy-4-alkoxybenzophenone to said compound is between 10/1 and 1/10.

* * * * *